United States Patent
Heyes

(10) Patent No.: US 8,007,741 B1
(45) Date of Patent: Aug. 30, 2011

(54) PIPETTING HEAD WITH PLATE GRIPPER

(75) Inventor: Kevin Heyes, Milpitas, CA (US)

(73) Assignee: SciGene Corporation, Sunnyvale, CA (US)

( * ) Notice: Subject to any disclaimer, the term of this patent is extended or adjusted under 35 U.S.C. 154(b) by 0 days.

(21) Appl. No.: 12/498,319

(22) Filed: Jul. 6, 2009

Related U.S. Application Data

(60) Provisional application No. 61/078,948, filed on Jul. 8, 2008.

(51) Int. Cl.
*B01L 3/02* (2006.01)

(52) U.S. Cl. ........ 422/511; 422/500; 422/501; 422/509; 422/524; 422/525

(58) Field of Classification Search ............... 73/864.01, 73/864.11, 864.13, 864.14, 864.23, 864.17, 73/864.24, 864.25, 864.31, 863.32, 863.31; 414/1, 4, 749.1, 751.1
See application file for complete search history.

(56) References Cited

U.S. PATENT DOCUMENTS

| | | | |
|---|---|---|---|
| 4,009,611 A * | 3/1977 | Koffer et al. | 73/864.14 |
| 4,952,518 A * | 8/1990 | Johnson et al. | 436/518 |
| 6,244,119 B1 * | 6/2001 | Theran | 73/864.17 |
| 2003/0215360 A1 * | 11/2003 | Ruddock | 422/63 |

* cited by examiner

*Primary Examiner* — Yelena G Gakh
*Assistant Examiner* — Christopher A Hixson
(74) *Attorney, Agent, or Firm* — Larry Guernsey; Patent Law Office of Larry Guernsey

(57) ABSTRACT

A pipetting head apparatus includes a pipetting system, and a gripper system, and which includes a floating gripper carriage, which is configured to move independently from said pipetting system. The pipetting system and said gripper system are configured to utilize a common motor. In alternative embodiment, a pipetting head apparatus includes a pipetting system, and a stripper assembly. The pipetting system and the stripper assembly are configured to utilize a common motor. In another alternative embodiment, a pipetting head apparatus includes a pipetting system, which includes a stripper assembly, a main carriage assembly, and a gripper assembly, where the stripper assembly and gripper assembly are both configured to move independently from the main carriage assembly. Also a method is disclosed for distributing material samples for laboratory processing.

22 Claims, 7 Drawing Sheets

PIPETTING HEAD WITH PLATE GRIPPER

The following is a non-provisional patent application which claims priority to provisional application 61/078,948 filed Jul. 8, 2008 by the same inventor.

TECHNICAL FIELD

The present invention relates generally to equipment for processing of laboratory specimens and more particularly to equipment for automated dispensing of materials for laboratory purposes.

BACKGROUND ART

Existing automated liquid handling systems in the biotechnology industry utilize pipette tips, syringes, or similar devices either as a single channel or in an array format for multiple channels. A pipetting apparatus is typically configured with a number of tubes fitted with pipetting tips, which then act as syringes to draw liquids into the tubes, and convey these samples to another array of containers, such as a multiwell plate, where they are then dispensed into the matching array of wells. Such an apparatus will be referred to as a "pipetting system".

Typical array configurations are 8×1, 12×1, 8×12, or 16×24, which refers to the number of rows and columns in the array. An apparatus which uses an 8×1 array is also referred to as an "8 Channel Head" and thus is configured to dispense materials into a multi-well plate having 8 wells in a row, and possibly multiple columns. The use of such automated systems eliminates much handling of materials, and as some of these materials are toxic or dangerous to handle, it is a great advantage that manual interaction with these materials is minimized.

It will be appreciated that once the materials have been dispensed into the multiwell plate by the pipetting apparatus, it is often desirable to have the loaded multiwell plate moved to a different location, perhaps for further processing, or perhaps merely to make room for other plates to be loaded. Once again, it is desirable to minimize human contact with these potentially hazardous materials, so further automated handling is generally desirable.

Therefore, automated liquid handling systems may incorporate some apparatus possibly referred to as a "gripper system" for picking up and moving containers from location to location on the instrument or for interacting with other instruments. Typically, the gripper system is a separate mechanism from those used to aspirate and dispense liquids through the pipetting system.

There is also a drive to condense the size of laboratory apparatus, as most small laboratories find counter space to be at a premium. Thus, any innovation that can reduce the "footprint" or space taken up on a counter is desirable. Having one discreet apparatus which is use for pipetting and another discreet apparatus which is then used for conveying the filled plates to another location requires that additional counter space must be utilized. A separate apparatus for conveyance also involves extra cost, as well as the necessity that the plate must be somehow transferred from a first apparatus to a second apparatus for conveyance, which involves risk of spillage or contamination.

Thus, there is a need for a pipetting apparatus which includes systems for dispensing materials and for gripping and conveying a plate in a single device.

DISCLOSURE OF INVENTION

An advantage of the present invention is that it includes both a pipetting system and a gripper system in a single device.

Another advantage of the present invention is that there is simplification of design, and therefore a reduction of parts.

And another advantage of the present invention is that it requires less counter space than separate and discreet apparatus for pipetting and conveying.

A further advantage of the present invention is that there is cost savings in performing the actions of aspirating/dispensing liquids, attaching/stripping pipette tips, and gripping/moving plates in a single device.

A yet further advantage is that less parts are required, primarily due to only a single motor and solenoid being used, which requires less electronics, wire harnesses, sensors, linear motion mechanical components, couplings, brackets, and related items.

An additional advantage of the present invention is that it presents a simple mechanical design, which is expected to be generally reliable.

Briefly, one preferred embodiment of the present invention is a pipetting head apparatus for distributing material samples for laboratory processing including a pipetting system, which includes a syringe array assembly; and a gripper system, and which includes a floating gripper carriage which is configured to move independently from the pipetting system. The pipetting system and said gripper system are configured to utilize a common motor.

Another preferred embodiment is a pipetting head apparatus for distributing material samples for laboratory processing, which includes a pipetting system, which includes a plunger movement assembly and a main carriage assembly. The plunger movement assembly is configured to move independently from the main carriage assembly. Also included is a stripper assembly which is also configured to move independently from the main carriage assembly. The pipetting system and the stripper assembly are configured to utilize a common motor to drive the pipetting system and the stripper assembly.

Another preferred embodiment is a pipetting head apparatus for distributing material samples for laboratory processing, which includes a pipetting system, which includes a stripper assembly and a main carriage assembly, where the stripper assembly is configured to move independently from said main carriage assembly. Also included is a gripper assembly, which is also configured to move independently from the main carriage assembly.

Also included is a method for distributing material samples for laboratory processing.

These and other advantages of the present invention will become clear to those skilled in the art in view of the description of the best presently known mode of carrying out the invention and the industrial applicability of the preferred embodiment as described herein and as illustrated in the several figures of the drawings.

BRIEF DESCRIPTION OF THE DRAWINGS

The purposes and advantages of the present invention will be apparent from the following detailed description in conjunction with the appended drawings in which.

BEST MODE FOR CARRYING OUT THE INVENTION

Figure 1:
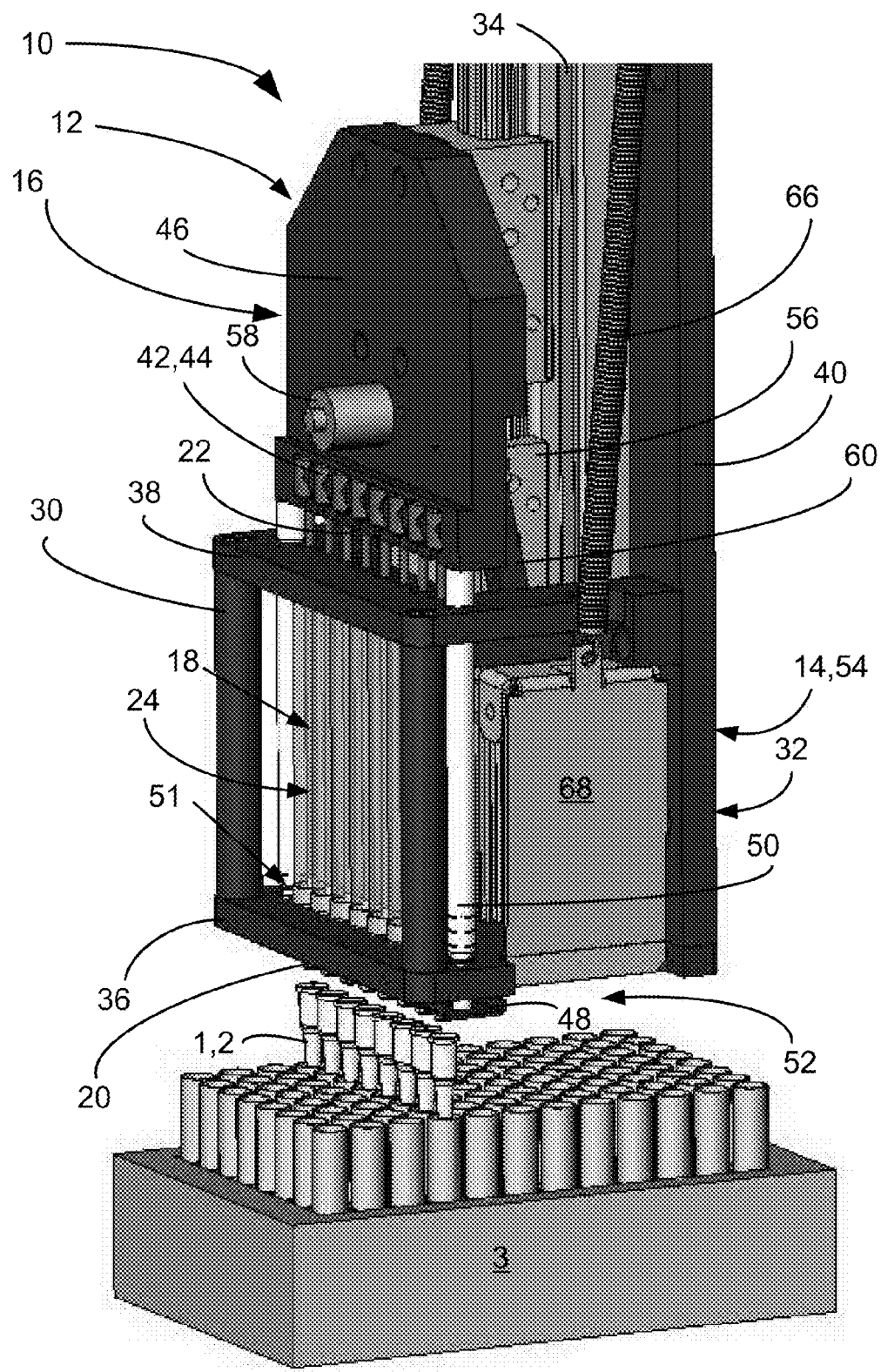
FIG. 1 shows a front isometric view of the pipetting head apparatus of the present invention.

The present invention is a pipetting head with integral plate gripping apparatus, which for purposes of this application will be referred to as pipetting head apparatus 10. In the following discussion, FIGS. 1-7 will be referred to generally. FIG. 1 shows a front isometric view of the pipetting head apparatus 10 and its major sub-systems. The pipetting head apparatus 10 includes generally a pipetting system 12 and a gripper system 14 which are combined in a single apparatus. As referred to above, this configuration has many advantages over systems, which use separate and discreet apparatuses for pipetting and gripping.

The pipetting system 12 generally includes a plunger movement assembly 16, a syringe array assembly 28 and a main carriage assembly 32, parts of which are also used by the gripper system 14, and also a pipette tip stripper assembly 52.

The pipetting system 12 functions to automatically engage, or disengage, a number of pipetting tips 1, which are usually stored in an array 2 in a pipetting tip rack 3. Once pipette tips 1 are mounted, liquids may be aspirated or dispensed into a variety of containers, usually microplates or tubes.

The pipetting system 12 includes a number of tubes 18 (currently 8 is preferred), each with a nozzle 20, and each tube 18 is fitted with a plunger 22. These tubes 18 are arranged in a tube array 24, whose spacing is aligned with the spacing of the pipetting tip array 2. Pipette tips 1 are attached to the tubes 18 by a force fit of the nozzles 20 into the pipette tips 1. The pipetting tips 1 are thus fitted to the nozzles 20 at the lower ends of the tubes 18 to form complete syringes 26, which are arranged in syringe array assembly 28.

The syringe array assembly 28 is held in a frame 30 which is part of a main carriage assembly 32, which moves up and down relative to the pipetting tip rack 3. As will be discussed below, the main carriage assembly 32 can move either in unison or independently of the plunger movement assembly 16. The frame 30 includes a bottom plate 36, which holds the nozzles 20 of the syringes 26 in place and an upper plate 38, which holds the upper ends of the tubes 18. The frame 30 is attached to the backplate 40, which is itself moved up and down by the placement system 78.

Each of the plungers 22 include an enlarged end 42, which is captured in a recess 44 formed in the plunger plate 46. Thus, relative motion of the main carriage assembly 32 compared to the plunger plate 46, allows the plungers ends 42 to be drawn upward relative to the nozzles 20, thus drawing up the plunger 22 within the tube 18 to aspirate or fill the syringes 26. Conversely, the plunger plate 46 can be moved downwards relative to the main carriage assembly 32 to depress toward the nozzles 20, thus advancing the plunger 22 within the tube 18 to evacuate the syringe 26. This relative motion is achieved by movement of the plunger plate 46 on a track 34, which is mounted on the backplate 40 of the main carriage assembly 32.

Thus, the plunger movement assembly 16 includes the plunger plate 46, with recesses 44 and track 34, and by activation of the motor 76, (see FIG. 6) the plunger assembly 16 can be driven up and down independently of the main carriage assembly 32 and thus also independent of the syringe array assembly 28.

In addition, a stripper plate 48 is positioned between the nozzles 20 and the pipetting tips, which are mounted onto the nozzles 20. This stripper plate 48 is connected to the lower ends of two stripper shafts 50. The upper ends of the stripper shafts 50 can be contacted by the plunger plate 46. Thus, further downward motion of the plunger plate 46 relative to the main carriage assembly 32 forces the stripper plate 48 downwards against the pipetting tips 1, thus forcing the pipetting tips 1 off of the nozzles 20, where they are preferably caught by a pipetting tip rack 3, thus "stripping" them from the nozzles 20. When not engaged in stripping operations, the stripper plate 48 is held in the "up" position by springs 51.

Thus, the stripper assembly 52 includes the stripper plate 48, stripper shafts 50 and springs 51. The movement of the stripper assembly 52 is controlled by the same plunger plate 46 that drives the plunger movement assembly 16.

The present pipetting head apparatus 10 includes a plate gripping system 14 by utilizing a gripper assembly 54 which includes a floating gripper carriage 56. The gripper carriage "floats" on track 34 and is biased upwards by springs 66.

The pipetting head apparatus 10 is able to operate this gripper assembly 54 through a solenoid 58 which activates a lever 60 that contacts the floating gripper carriage 56. This is best seen through a comparison of FIGS. 2 and 3, which are both plan side views of the plunger plate 46 and floating gripper carriage 56, with FIG. 2 showing the gripper assembly 54 retracted and disengaged from gripping a plate, and FIG. 3 showing the gripper assembly 54 extended and gripping a multi-well plate 4.

Figure 2:
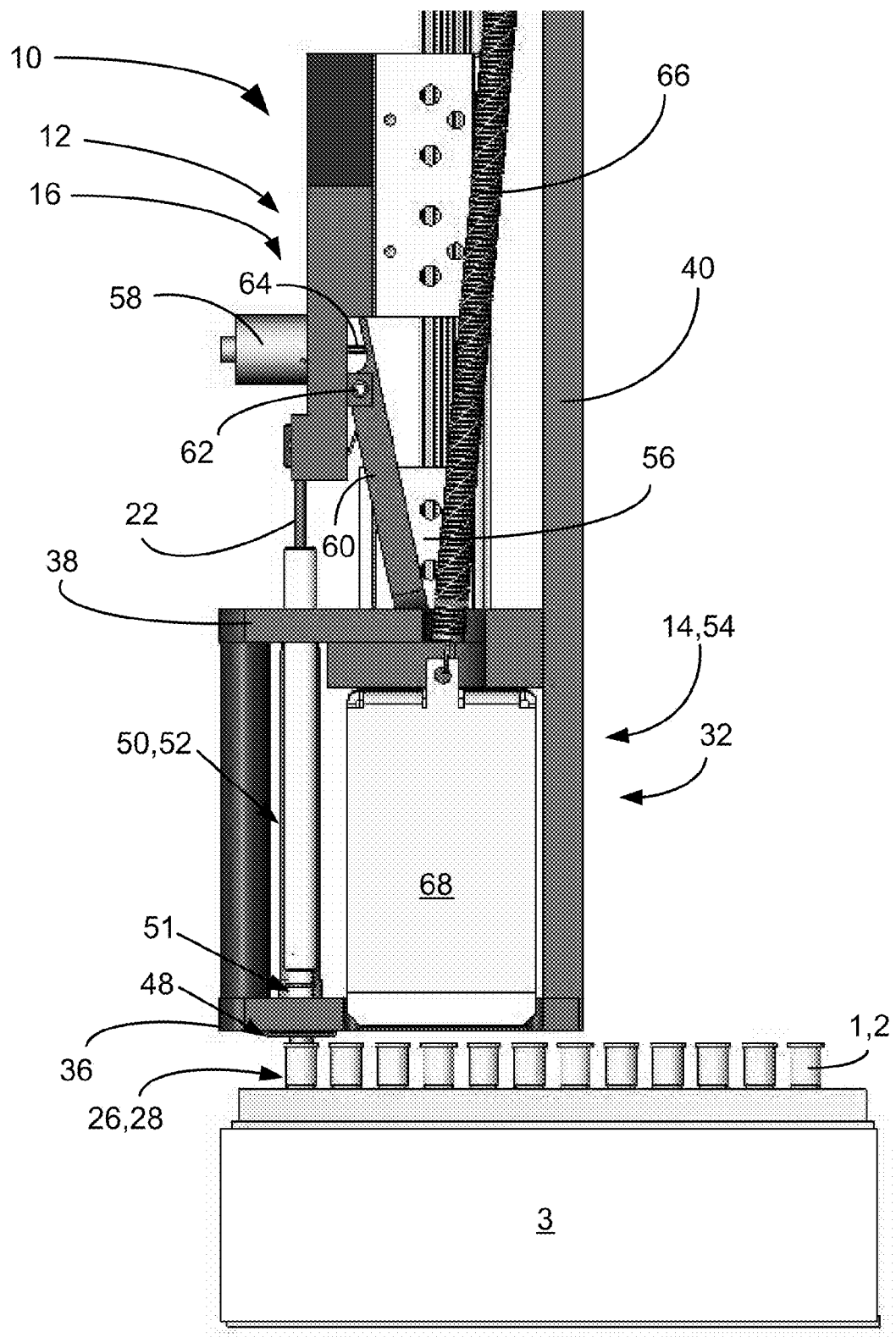
FIG. 2 shows a side plan view of a portion of the pipetting head apparatus of the present invention with the plate gripper retracted.

Thus, FIG. 2 shows the gripper system 14 not in use, as the solenoid 58 is not activated. The lever 60 is designed to pivot about pivot 62. The lower end of the lever 60 contacts the floating gripper carriage 56, but does not press on it when the gripper system 14 is not in use.

Figure 3:
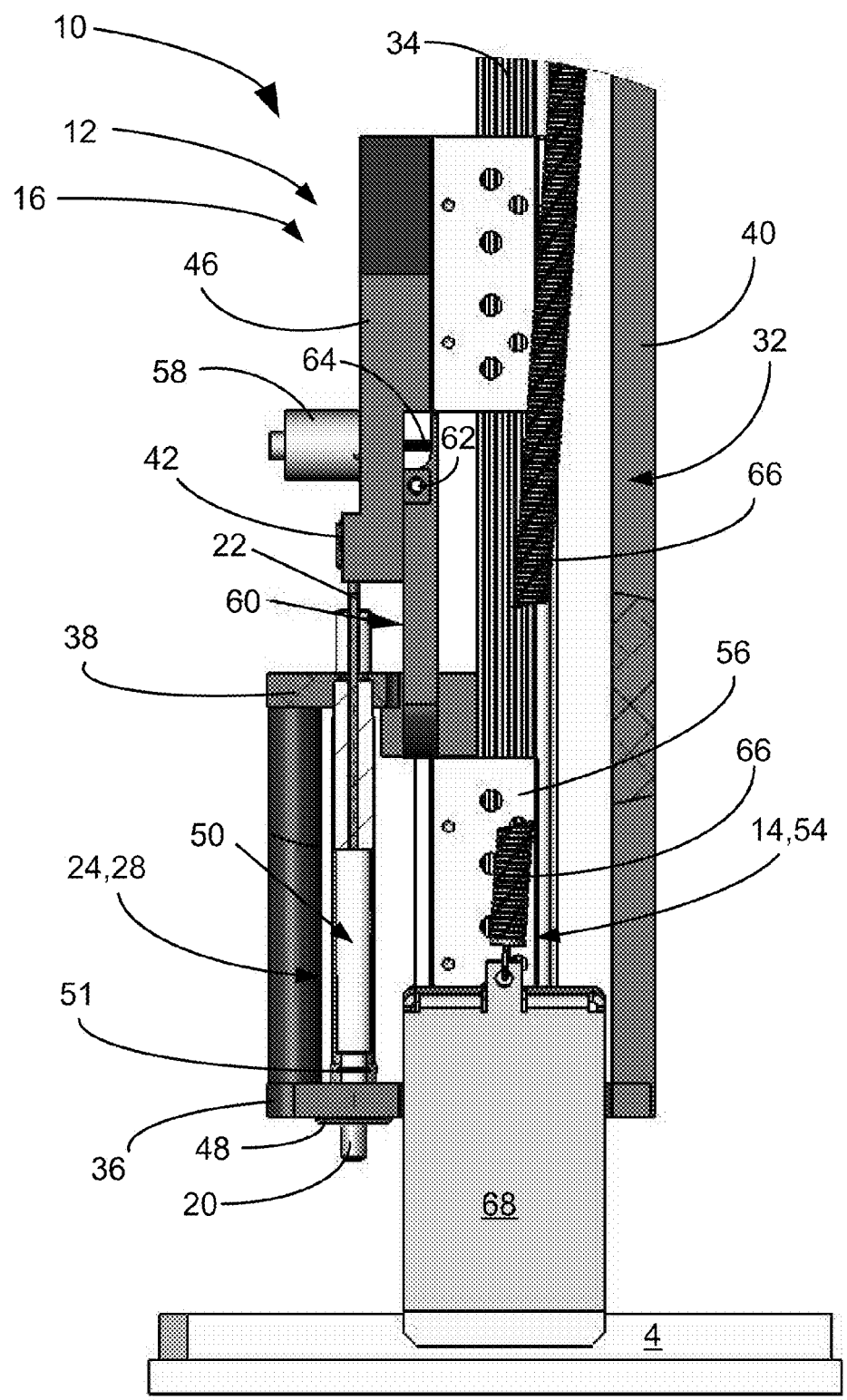
FIG. 3 shows a side plan view of a portion of the pipetting head apparatus of the present invention with the plate gripper extended.
Figure 4:
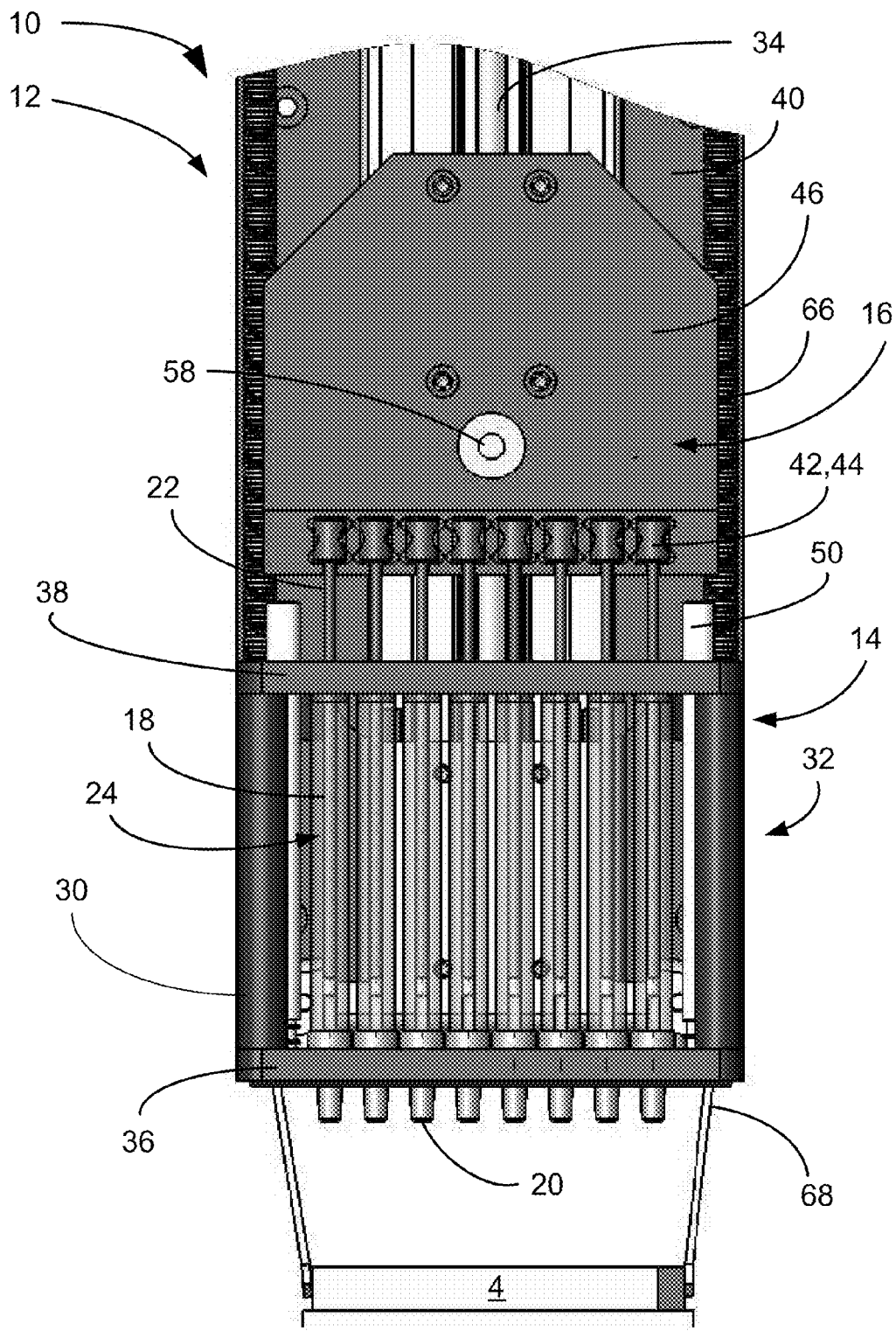
FIG. 4 shows a front plan view of a portion of the pipetting head apparatus of the present invention with the plate gripper extended.

In FIG. 3, the solenoid 58 has been activated, causing a pin 64 to extend, pressing on the upper end of the lever 60. The lever 60 thus rotates clockwise in this figure about pivot 62. The lower end of the lever 60 engages the floating gripper carriage 56. The motor 76 (see FIG. 6) then activates, moving the plunger plate 46, and the gripper assembly 54 downwards on the track 34, against the urgings of springs 66 which are attached to the upper portions of the gripper fingers 68. Note that a middle portion of the springs is not included in FIG. 3 to provide a clearer view.

Figure 5:
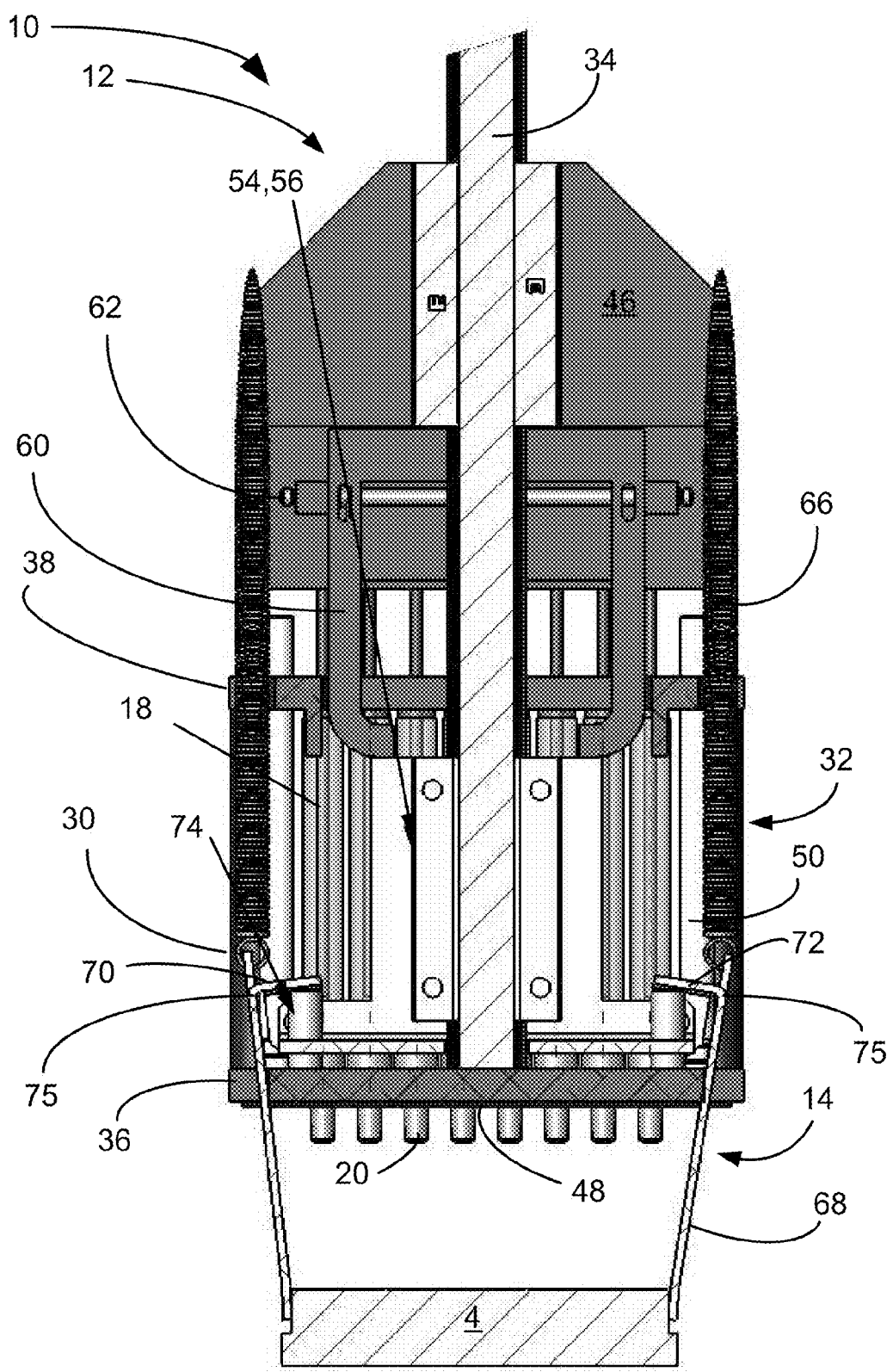
FIG. 5 shows a rear plan view, with the backplate removed, of a portion of the pipetting head apparatus of the present invention with the plate gripper extended.
Figure 6:
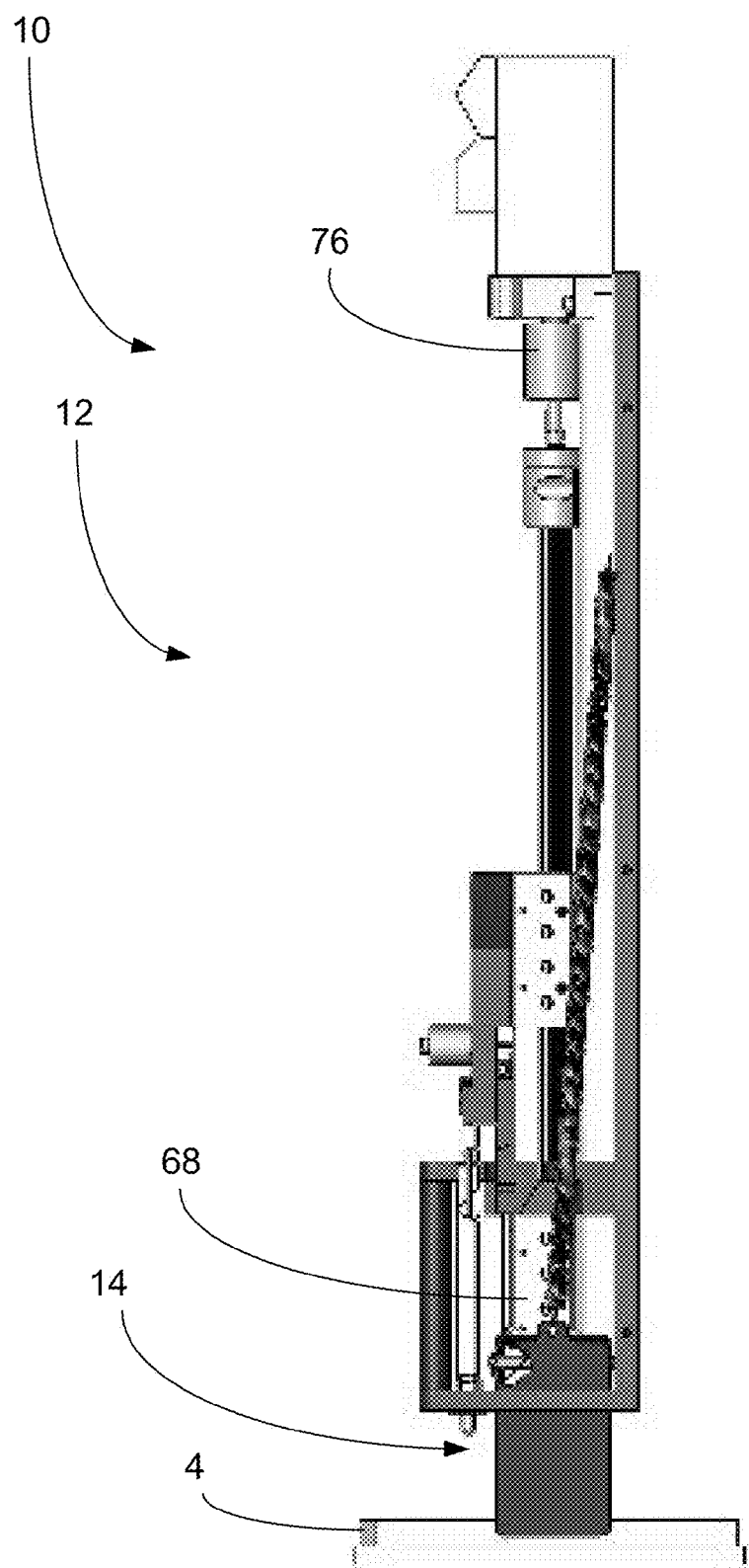
FIG. 6 shows an expanded side plan view of the pipetting head apparatus of the present invention including motors.

Referring now also to FIGS. 5 and 6, the upper ends 70 of the gripper fingers 68 preferably include angled portions 72, which contact gripper pins 74. The gripper fingers 68 travel generally straight downwards until the angled portions 72 of the fingers 68 contact the gripper pins 74. Contact between the angled portions 72 and these gripper pins 74 causes the gripper fingers 68 to rotate inward about gripper pivots 75 as they continue to lower, thus causing the gripper fingers 68 to close in upon the plate 4, thus gripping it. Placement system 78 can then move the entire pipetting head apparatus 10 with plate 4 in gripper, to another location on baseplate 80.

Opening the gripper fingers 68 is simply a matter of reversing the direction of the gripper assembly 54. When not in use, the gripper fingers 68 are retracted behind the syringe array assembly 28 by the action of the springs 66, so that no interference will occur as the pipetting system 12 is picking up or stripping off pipette tips 1. The lever 60 pivots to its original position by deactivating the solenoid. A spring (not shown) presses on the lower end of the lever rotating it counterclockwise.

Thus, the plunger plate 46 can move along with the main carriage assembly 32, or it can move independently from the main carriage assembly 32, and the gripper assembly 54 can be activated to move along with the plunger plate 46. Therefore, there are basically four modes of motion of the syringe array assembly on the main carriage assembly that are activated at various stages of the processing operation, namely 1) plunger plate and syringe array assembly move together, 2) the plunger plate moves independently from the syringe array assembly to depress or draw upwards plungers, 3) the plunger plate moves together with the gripper assembly to grip a plate, and 4) the plunger plate moves independently from the syringe array assembly so that the stripper assembly is activated to push off the pipetting tips.

When the syringe assembly is receiving new pipette tips, the plunger plate 46 and syringe array assembly 28 move downwards together to force-fit the nozzles 20 of the syringes 26 into the mouths of the pipette tips 1, and then the syringe array assembly 28 and plunger plate 46 move upwards together again, thus exhibiting the first mode of motion.

The pipetting head assembly 10 is positioned over a microwell plate 4 or other sample container to either aspirate (draw up) material, or to dispense material. The pipetting tips 1 are positioned to match the wells of the well plate, and as the syringe array assembly 28 remains stationary, the plunger plate 46 either rises up pulling the syringe plunger ends 42 upward to aspirate, or the plunger plate 46 moves downward pushing the plunger ends 42 downward to dispense liquid from the syringes 26 into the wells or containers. This exhibits the second mode of motion.

The third mode of motion is exhibited when the pipetting head apparatus 10 is positioned over a plate 4, the solenoid 58 is activated so that the lever 60 engages the floating gripper carriage assembly 56 and moves it downward, as the plunger plate 46 descends. The angled portions 72 of the fingers 68 contact the gripper pins 74 causing the gripper fingers 68 to rotate inward and to close in upon the plate 4, thus gripping it.

The fourth mode of motion occurs when the pipetting head apparatus 10 is preferably positioned over a pipetting tip rack 3 to strip off the tips 1. The main carriage assembly 32 and thus the syringe array assembly 28 lowers with the plunger plate 46. The main carriage assembly 32 stops, and the plunger plate 46 continues downward until it contacts the stripper shafts 50, which then force the stripper plate 48 to push the pipetting tips 1 off of the nozzles 20 into the pipetting tip rack 3.

Figure 7:
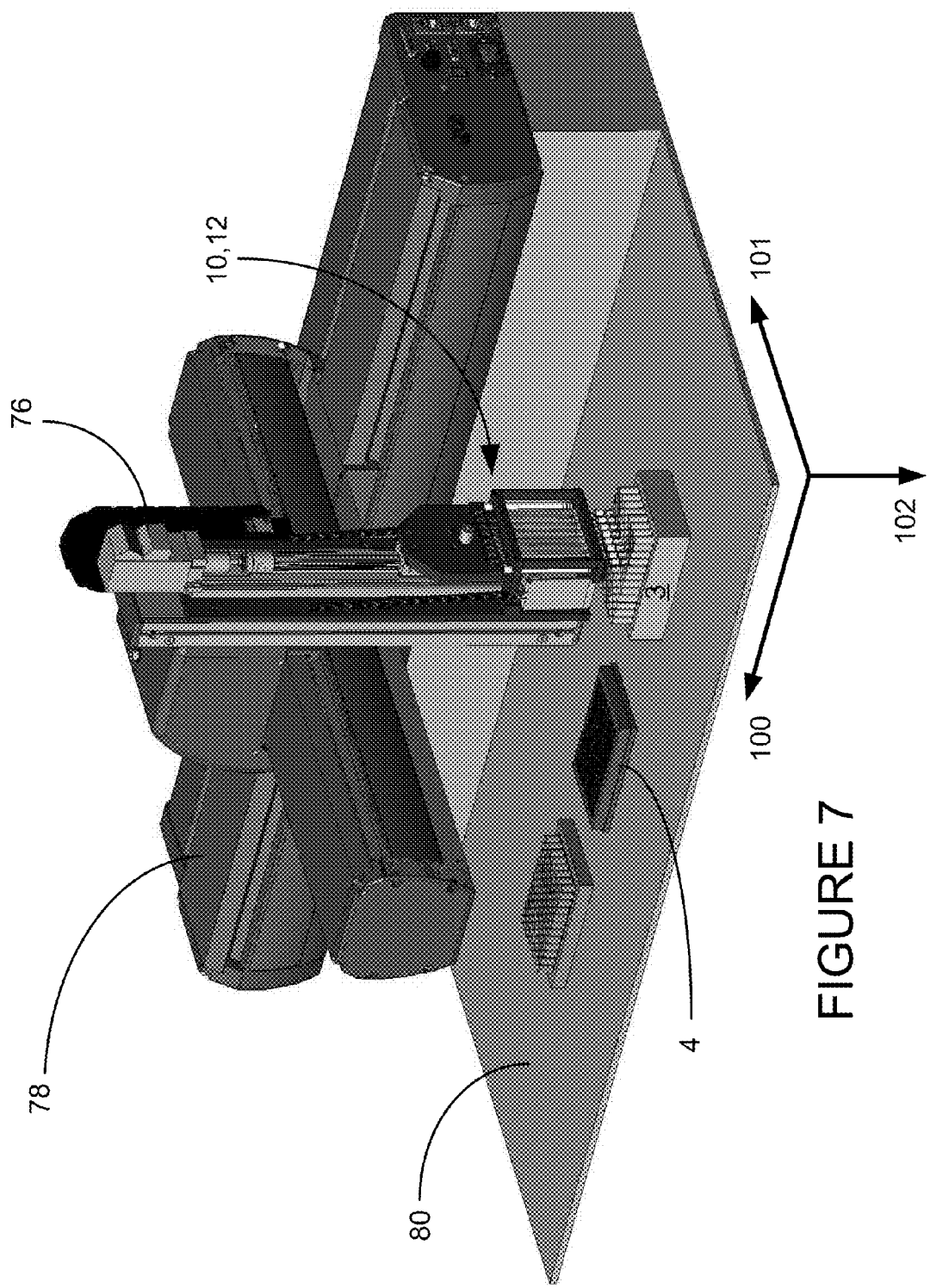
FIG. 7 shows an isometric view of the pipetting head apparatus of the present invention in use with a placement assembly.

FIG. 7 shows the pipetting head apparatus 10 including the pipetting system 12 in use with a placement system 78, which is generally configured as a robotic arm or other mechanism. Motors in the placement system 78 move the pipetting head apparatus 10 in position over a baseplate 80, which can support a pipetting tip rack 3, a multiwell plate 4 or a pipetting tip disposal rack 5. Thus motors in the placement system 78 can provide movement in the X-axis direction 100, the Y-axis direction 101, and the vertical Z-axis 102 direction. Additionally, the motor 76 in the pipetting head apparatus 10 provides movement in the vertical Z-axis 102 direction for moving the plunger plate 46 to aspirate/dispense liquids and for lowering/opening/closing the gripper fingers 68, and stripping tips 1 from nozzles 20.

As discussed above, the advantages of the pipetting head apparatus 10 are seen in the simplification of design, reduction of parts, reduced space requirements, and cost savings for equipment necessary to perform the actions of aspirating/dispensing liquids, attaching/stripping pipette tips, and gripping/moving plates. Fewer parts are required, primarily due to using a single motor and solenoid. This requires less electronics, wire harnesses, sensors, linear motion mechanical components, couplings, brackets, and related items. Simpler mechanical designs are generally more reliable and enhanced reliability is expected in this invention as well.

While various embodiments have been described above, it should be understood that they have been presented by way of example only, and not limitation.

INDUSTRIAL APPLICABILITY

The present invention is a pipetting head apparatus 10. The pipetting head apparatus 10 includes generally a pipetting system 12 and a gripper system 14 which are combined in a single apparatus.

The pipetting system 12 generally includes a plunger movement assembly 16, a syringe array assembly 28 and a main carriage assembly 32, parts of which are also used by the gripper system 14, and also a pipette tip stripper assembly 52.

Relative motion of the main carriage assembly 32 compared to the plunger plate 46, allows the plungers ends 42 to be drawn upward relative to the nozzles 20, thus drawing up the plunger 22 within the tube 18 to aspirate or fill the syringes 26. Conversely, the plunger plate 46 can be moved downwards relative to the main carriage assembly 32 to depress toward the nozzles 20, thus advancing the plunger 22 within the tube 18 to evacuate the syringe 26. This relative motion is achieved by movement of the plunger plate 46 on a track 34 which is mounted on the backplate 40 of the main carriage assembly 32.

A stripper plate 48 is positioned between the nozzles 20 and the pipetting tips, which are mounted onto the nozzles 20. The movement of the stripper assembly 52 is controlled by the same plunger plate 46 that drives the plunger movement assembly 16.

The present pipetting head apparatus 10 includes a plate gripping system 14 by utilizing a gripper assembly 54 which includes a floating gripper carriage 56. The gripper carriage "floats" on track 34 and is biased upwards by springs 66.

The pipetting head apparatus 10 is able to operate this gripper assembly 54 through a solenoid 58 which activates a lever 60 that contacts the floating gripper carriage 56.

Thus, the plunger plate 46 can move along with the main carriage assembly 32, or it can move independently from the main carriage assembly 32, and the gripper assembly 54 can be activated to move along with the plunger plate 46.

Speaking generally, in a typical operation cycle, the pipetting head apparatus carries out the operations of gripping and placing a target plate to which materials will be dispensed, mounting a clean set of pipetting tips to its syringe array, aspirating material from a first material source into its syringes, returning to the target plate, and dispensing the aspirated material. The pipetting tips are then automatically stripped from the syringe array, and new tips installed, if further cycles of aspiration and dispensing to the target plate are to be done. Once the final dispensing and stripping of tips for this cycle is complete, the target plate is gripped and placed for further processing, storage or disposal.

Speaking more specifically, the pipetting head apparatus 10 will be assumed to place and dispense materials to a multiwell plate 4 in the following discussion. Among others, FIG. 7 will be referred to.

Motors in the placement system 78 move the pipetting head apparatus 10 in position over a multiwell plate 4, on a baseplate 80. The plunger plate 46 is moved upwards by motor 76, and the solenoid 58 is activated so that the lever 60, rotating about pivot 62, is in position to engage the floating gripper carriage assembly 56 and moves it downward also, as the plunger plate 46 descends. The angled portions 72 of the fingers 68 contact the gripper pins 74 causing the gripper fingers 68 to rotate inward about gripper pivot 75 and to close in upon the plate 4, thus gripping it.

The pipetting head apparatus 10, including the main carriage assembly 32, is then raised up on the Z-axis 102, lifting the gripped multiwell plate 4. The motors in the placement system 78 provide movement in the X-axis direction 100, the Y-axis direction 101, and the Z-axis direction 102 until the multiwell plate 4 is in the appropriate location to place it on the baseplate 80.

The gripper fingers 68 are then opened by the action of motor 76 moving the plunger plate 46 upwards, thus reversing the direction of the gripper assembly 54, and are then retracted behind the syringe array assembly 28 by the action of the springs 66. The lever 60 pivots to its original position by deactivating the solenoid. A spring (not shown) presses on the lower end of the lever rotating it counter-clockwise. The multiwell plate 4 is thus placed at the desired location on the baseplate 80.

The pipetting head apparatus 10 then moves to receive new pipette tips for the syringe array assembly 28 by again using the motors in the placement system 78 to move to the correct X and Y coordinates of a pipetting tip array 3, as seen in FIG. 7. The syringe array assembly 28, attached to the main carriage assembly 32 is then lowered by action of the motor 76 so that the syringe array assembly 28 moves downward to force-fit the nozzles 20 of the syringes 26 into the mouths of the pipette tips 1. Then the syringe array assembly 28 is moved upwards, carrying the pipette tips 1.

The pipetting head assembly 10 is then positioned by the placement system 78 over a sample container (not shown), or other source of material to be dispensed, to aspirate material, which will be dispensed into the wells of the microwell plate 4 previously positioned. The ends of the pipetting tips 1 are inserted into the sample container, and as the syringe array assembly 28 remains stationary, the plunger plate 46 rises up pulling the syringe plunger ends 42 upward to aspirate liquid into the syringes 26 through the action of motor 76.

The pipetting head assembly 10 is then positioned by the placement system 78 over the microwell plate 4 previously positioned, and material is dispensed into the wells of the microwell plate 4. The pipetting tips 1 are positioned to match the wells of the multiwell plate 4, and as the syringe array assembly 28 remains stationary, the action of motor 76 causes the plunger plate 46 to move downward pushing the plunger ends 42 downward to dispense liquid from the syringes 26 into the wells of the multiwell plate 4.

When the dispensing of material is completed, the pipetting head apparatus 10 is then preferably positioned over a pipetting tip disposal rack 5 to strip off the tips 1. The main carriage assembly 32, and thus the syringe array assembly 28, lowers with the plunger plate 46. The main carriage assembly 32 stops, and the plunger plate 46 continues downward until it contacts the stripper shafts 50, which then force the stripper plate 48 to push the pipetting tips 1 off of the nozzles 20 into the pipetting tip disposal rack 5.

The cycle of fitting pipette tips 1, aspirating, dispensing, and removing pipette tips 1 may be repeated one or more times if other materials are to be added to the wells of the multiwell plate 4 previously positioned.

The pipetting head apparatus 10 can again lower and grip the multiwell plate 4 by the process described above, and lift it to be placed and then released at its next location, perhaps for storage, further processing, cleaning or disposal.

As discussed above, the advantages of the pipetting head apparatus 10 are seen in the simplification of design, reduction of parts, reduced space requirements, and cost savings for equipment necessary to perform the actions of aspirating/dispensing liquids, attaching/stripping pipette tips, and gripping/moving plates. Fewer parts are required, primarily due to using a single motor and solenoid. This requires less electronics, wire harnesses, sensors, linear motion mechanical components, couplings, brackets, and related items. Simpler mechanical designs are generally more reliable and enhanced reliability is expected in this invention as well.

For the above and other reasons it is expected that the present pipetting head apparatus 10 of the present invention will have widespread industrial applicability. Therefore, it is expected that the commercial utility of the present invention will be extensive and long lasting.

What is claimed is:

1. A pipetting head apparatus for distributing material samples for laboratory processing, comprising:
   a pipetting system, which includes a syringe array assembly; and
   a gripper system, which includes a floating gripper carriage which is configured to move independently from said pipetting system;
   wherein said pipetting system and said gripper system are configured to utilize a common motor to operate said pipetting system and to operate said gripper system wherein said pipetting head apparatus further includes a lever which is activated by a solenoid to pivot to a position where said lever activates said gripper system.

2. The pipetting head apparatus of claim 1, wherein said syringe array assembly includes a plurality of tubes, and where said pipetting system further includes a plunger movement assembly by which a plurality of plungers are moved within said tubes of said syringe assembly.

3. The pipetting head apparatus of claim 2, wherein said plunger movement assembly includes a plunger plate by which said plungers are moved.

4. The pipetting head apparatus of claim 3, wherein said pipetting head apparatus includes a main carriage assembly, and wherein said plunger movement assembly is configured to move independently from said main carriage assembly.

5. The pipetting head apparatus of claim 4, wherein said pipetting head apparatus includes a stripper assembly, whereby pipetting tips are disengaged from said tubes, and wherein said stripper assembly is configured to move independently from said main carriage assembly.

6. The pipetting head apparatus of claim 5, wherein said stripper assembly includes a stripper plate and stripper shafts which contact said stripper plate, and wherein pressure of said plunger plate on said stripper shafts in turn presses said stripper plate to disengage said pipette tips from said tubes.

7. The pipetting head apparatus of claim 3, wherein said pipetting head apparatus includes a main carriage assembly, and wherein said gripper system is configured to move independently from said main carriage assembly.

8. The pipetting head apparatus of claim 7, wherein said gripper system includes gripper fingers which are configured to grip a plate in response to pressure by said plunger plate.

9. The pipetting head apparatus of claim 8, wherein said lever which is activated by a solenoid to activate said gripper system pivots to a position where said lever engages said gripper fingers and urges said gripper fingers to grip a plate in response to pressure by said plunger plate.

10. The pipetting head apparatus of claim 4, wherein said main carriage assembly includes a track on which said plunger plate is moved by said motor.

11. A pipetting head apparatus for distributing material samples for laboratory processing, comprising:
a pipetting system, which includes a plunger movement assembly and a main carriage assembly wherein said plunger movement assembly is configured to move independently from said main carriage assembly; and
a gripper system which is also configured to move independently from said main carriage assembly;
wherein said plunger movement assembly and said gripper system are configured to utilize a common motor to operate said plunger movement assembly and to operate said gripper system, and wherein said pipetting head apparatus further includes a lever which is activated by a solenoid to pivot to a position where said lever activates said gripper system.

12. The pipetting head apparatus of claim 11, wherein said pipetting system includes a syringe array assembly, which includes a plurality of tubes, and wherein said plunger movement assembly includes a plunger plate, by which a plurality of plungers are moved within said tubes of said syringe array assembly.

13. The pipetting head apparatus of claim 12, further comprising a stripper assembly which includes a stripper plate and stripper shafts which contact said stripper plate, and wherein pressure of said plunger plate on said stripper shafts in turn presses said stripper plate to disengage said pipette tips from said tubes.

14. The pipetting head apparatus of claim 12, where said gripper system includes gripper fingers, which are configured to grip a plate.

15. The pipetting head apparatus of claim 14, wherein said lever which is activated by a solenoid to activate said gripper system pivots to a position where said lever engages said gripper fingers and urges said gripper fingers to grip a plate in response to movement by said plunger plate.

16. The pipetting head apparatus of claim 13, wherein said gripper system is configured to be operated by said motor which is configured to operate also both said plunger movement assembly and said stripper assembly.

17. A pipetting head apparatus for distributing material samples for laboratory processing, comprising:
a pipetting system, which includes a stripper assembly and a main carriage assembly wherein said stripper assembly is configured to move independently from said main carriage assembly;
a gripper system which is also configured to move independently from said main carriage assembly: and
a motor;
wherein said stripper assembly and said gripper system are configured to be operated by the same said motor and wherein said pipetting head apparatus further includes a lever which is activated by a solenoid to pivot to a position where said lever activates said gripper system.

18. The pipetting head apparatus of claim 17 wherein:
said pipetting system further comprises a syringe array assembly including a plurality of tubes, and where said pipetting system further includes a plunger movement assembly by which a plurality of plungers are moved within tubes of said syringe assembly, and wherein said plunger movement assembly includes a plunger plate.

19. The pipetting head apparatus of claim 18, wherein said stripper assembly includes a stripper plate and stripper shafts which contact said stripper plate, and wherein pressure of said plunger plate on said stripper shafts in turn presses said stripper plate to disengage said pipette tips from said tubes.

20. The pipetting head apparatus of claim 19, further comprising a gripper system which includes gripper fingers, which are configured to grip a plate.

21. The pipetting head apparatus of claim 20, wherein said lever which is activated by a solenoid to activate said gripper system pivots to a position where said lever engages said gripper fingers and urges said gripper fingers to grip a plate in response to movement by said plunger plate.

22. The pipetting head apparatus of claim 17, wherein said gripper system is configured to be driven by a motor which is configured to operate also both said plunger movement assembly and said stripper assembly.

* * * * *